United States Patent [19]
Packer et al.

[11] 3,968,797
[45] July 13, 1976

[54] DISPOSABLE DOUCHE PRODUCT

[75] Inventors: Gilbert Packer; Roger W. Boucher, both of Bristol; James M. Moore, East Greenwich, all of R.I.; John D. Wark, Freeport; Henry A. Holzwarth, Bayside, both of N.Y.

[73] Assignee: International Paper Company, New York, N.Y.

[22] Filed: Aug. 13, 1974

[21] Appl. No.: 497,122

[52] U.S. Cl. .................... 128/232; 128/251
[51] Int. Cl.² .......................... A61M 1/00
[58] Field of Search ........ 128/232, 225, 251, 247, 128/239

[56] References Cited
UNITED STATES PATENTS

| | | | |
|---|---|---|---|
| 2,623,519 | 12/1952 | Cohen | 128/225 UX |
| 2,766,913 | 10/1956 | Wilshosen | 128/225 UX |
| 2,818,863 | 1/1958 | Hoffman et al. | 128/251 |
| 2,881,760 | 4/1959 | McGiveran et al. | 128/251 |
| 2,888,925 | 6/1959 | Philips | 128/251 |
| 3,010,454 | 11/1961 | Lucie et al. | 128/239 X |
| 3,161,196 | 12/1964 | Berkow | 128/225 |
| 3,399,676 | 9/1968 | McLaughlin | 128/247 X |
| 3,507,280 | 4/1970 | Pollock | 128/232 |
| 3,688,766 | 9/1972 | Kempel | 128/232 |

FOREIGN PATENTS OR APPLICATIONS

| | | | |
|---|---|---|---|
| 372,786 | 4/1907 | France | 128/232 |
| 919,248 | 3/1947 | France | |
| 425,764 | 6/1924 | Germany | |
| 190,846 | 5/1937 | Switzerland | |

*Primary Examiner*—John D. Yasko
*Attorney, Agent, or Firm*—Finnegan, Henderson, Farabow & Garrett

[57] ABSTRACT

A douche nozzle adapted to be attached to a liquid container is disclosed which comprises an elongated tube having a passageway therethrough, a substantially conical base portion, means adapted to affix the base portion onto a container and a shield portion formed as a continuation of the base portion and adapted to overlap a portion of the container. A completely self-contained douche product is also disclosed which includes the nozzle and a flexible sealed container having a quantity of douching liquid sufficient for a single application.

46 Claims, 17 Drawing Figures

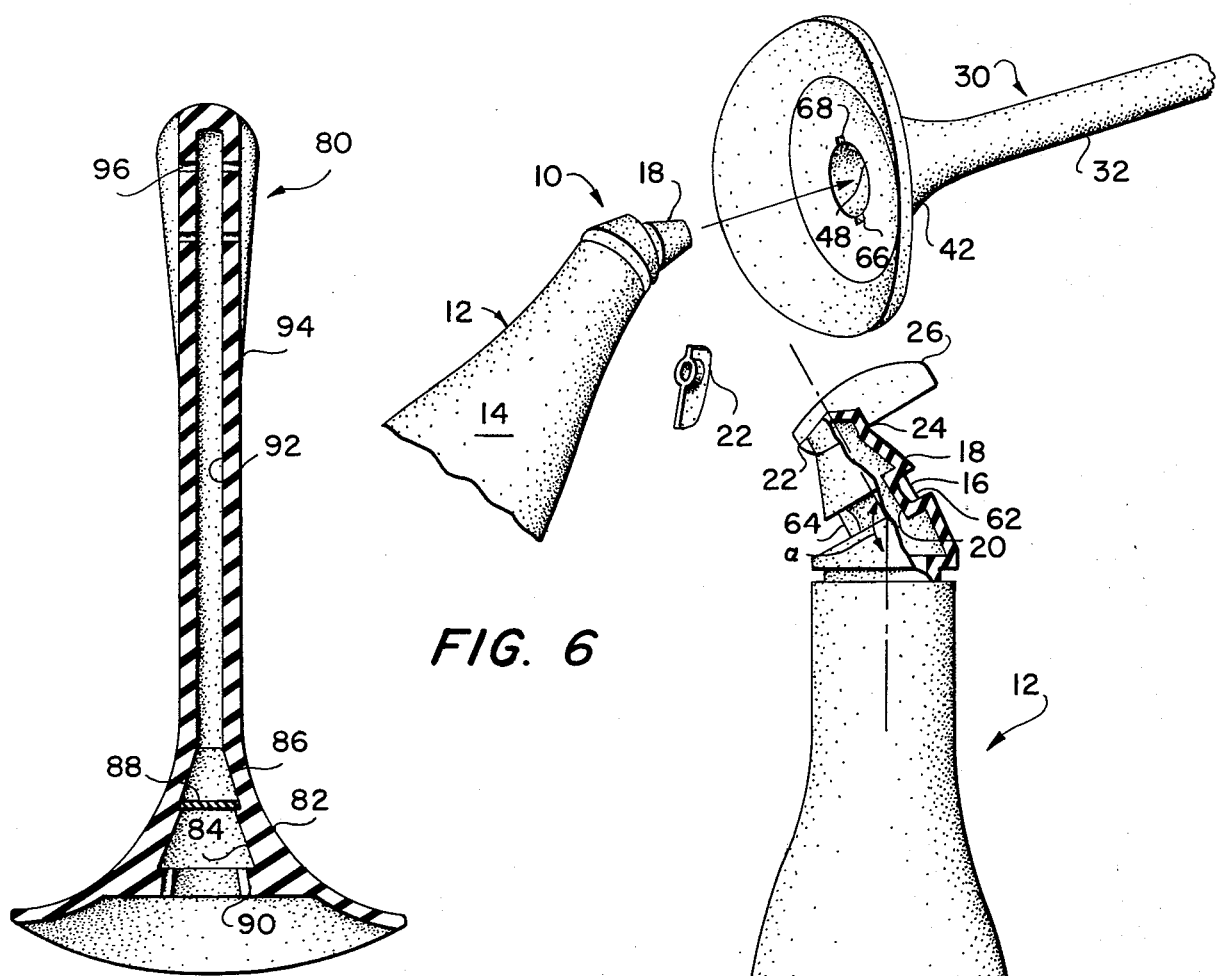
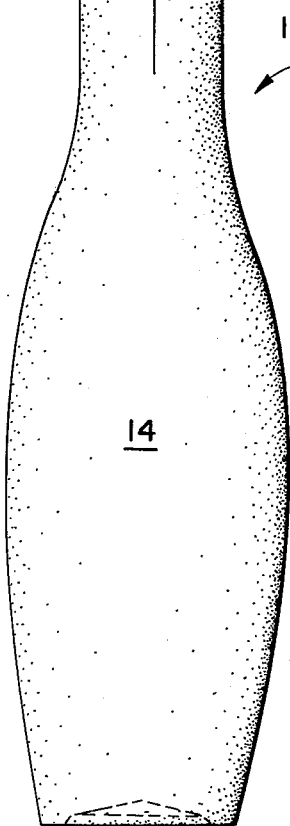
FIG. 2
FIG. 6
FIG. 7
FIG. 5
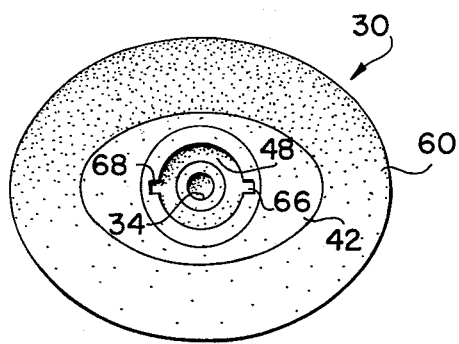

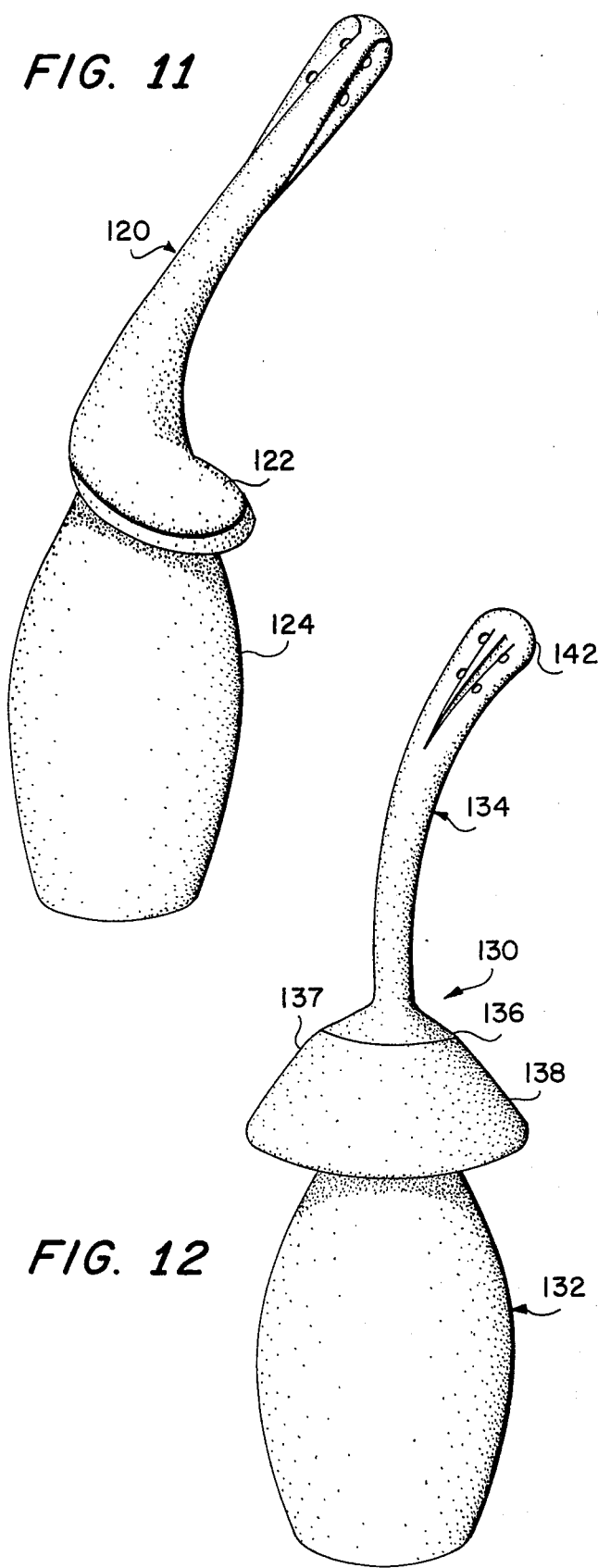
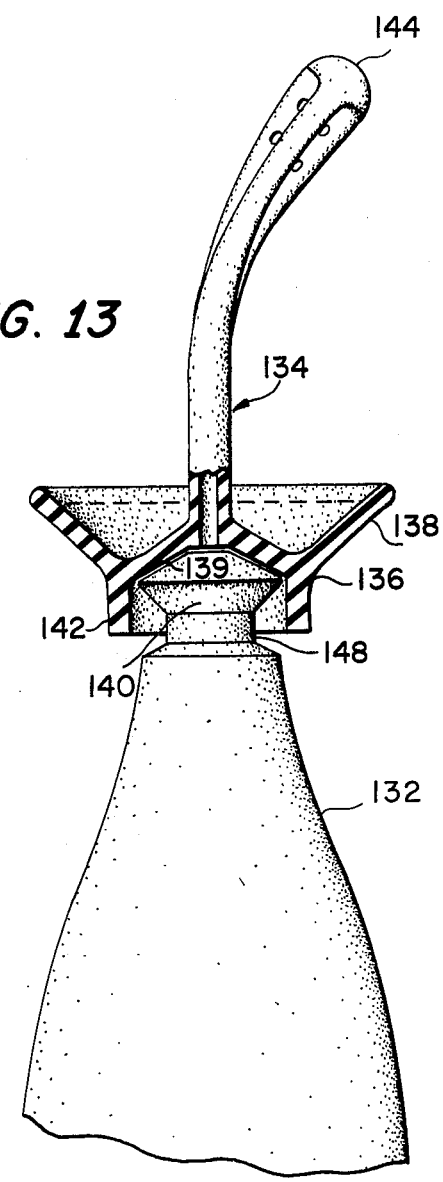
FIG. 11
FIG. 12
FIG. 13

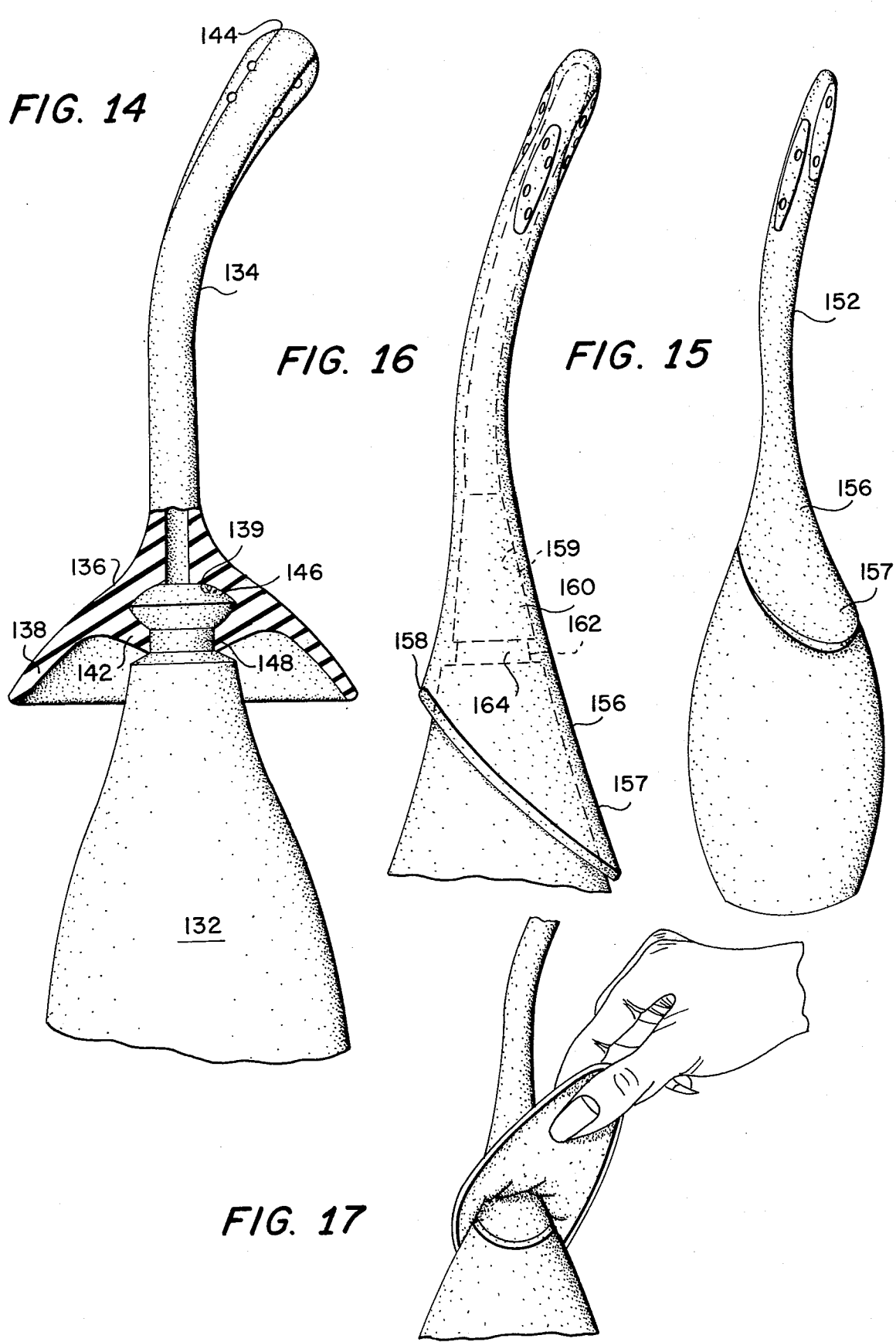

DISPOSABLE DOUCHE PRODUCT

BACKGROUND OF THE INVENTION

This invention relates to douching apparatus, and more particularly, to a totally self-contained, disposable douche product.

Conventional douching apparatus normally contains a reusable, flexible bag having an opening at one end, a tube adapted to be mounted on and removed from the bag and a nozzle attached to the distal end of the tube. In order to use a douching apparatus, the bag is manually filled with a liquid douching solution and the bag is then supported in an elevated position in order that the liquid may be gravity fed under sufficient pressure.

Use of this inventional douching is accompanied by many inconveniences. To begin with, the user must make the appropriate douching solution, usually by mixing a powder with a liquid in the bag. The bag must then be raised and mounted in an elevated position, which is not always convenient or easy to do. A clamp on the hose must be closed to avoid the solution from unintentionally escaping. When finished using the apparatus, it is necessary to carefully clean and store the apparatus since it is intended to be used repeatedly. This problem is compounded in institutional use, such as in hospitals, wherein the apparatus must be sterilized before each use.

A more convenient douching apparatus is formed of a resilient bulb having a pipe or nozzle extending therefrom. The user must make the appropriate solution and place it in a glass, evacuate the bulb by squeezing it, insert the nozzle in the solution and release the bulb to ingest the solution into the bulb. The apparatus is then ready for use and the liquid is expelled from the apparatus by squeezing the bulb. Both the nozzle and the bulb must be carefully cleaned and stored.

In addition to cleaning and storage, another inconvenience in using conventional douching apparatus is the tendency for the effluent douching solution to contact the user's legs and hands as it is being expelled from the body cavity into which the douching solution has been directed.

Accordingly, it is an an objective of this invention to provide a douche nozzle which is sufficiently inexpensive to manufacture as to permit it to be disposable and which is adapted to be easily attached to and removed from the liquid container.

It is another objective of this invention to provide a douche nozzle having a shield formed as an integral part thereof wherein the shield is contoured to direct the flow of effluent away from the user's body.

It is a further objective of this invention to provide a disposable douche product which is completely self-contained and ready for use and which includes an improved nozzle having a flow directing shield integrally formed thereon.

Additional objectives and advantages of the invention will be set forth in part in the description which follows and in part will be obvious from the description, or may be learned by practice of the invention. The objectives and advantages of the invention may be realized and attained by means of the instrumentalties and combinations particularly pointed out in the appended claims.

BRIEF DESCRIPTION OF THE INVENTION

To achieve the foregoing objectives in accordance with the purpose of the invention, as embodied and broadly described herein, the douche nozzle of this invention comprises an elongated tube having a passageway therethrough, at least one aperture through a first end of the tube communicating with the first passageway, a base portion formed at a second end of said tube remote from the first end, the base portion having a substantially conical configuration, a bottom wall, means adapted to affix the base portion onto a liquid container, and a shield portion formed as a continuation of the base portion, at least a section of the shield portion extending away from the first end and beyond the bottom wall and being adapted to overlap the container when mounted thereon.

Preferably, the means for affixing the base portion onto the liquid container includes a cavity within the base portion and means for releasably retaining the base portion on the container. It is also preferred that the tube and shield portion have a greater flexibility than the base portion.

The invention also comprises a disposable douche product including a douche nozzle described above and a flexible container having a head at one end with a passageway therethrough, removable means on the head to obturate the passageway and a douching liquid contained within the container, the quantity of liquid being suitable for a single douching application.

BRIEF DESCRIPTION OF THE DRAWINGS

The invention consists in the novel parts, constructions, arrangements, combinations and improvements shown and described. The accompanying drawings, which are incorporated in and constitute a part of this specification, illustrate several embodiments of the invention and, together with the description, serve to explain the principles of the invention.

In the drawings:

FIG. 2 is a partial sectional view of the liquid container of the douche product of FIG. 1.

FIG. 5 is a bottom view of the nozzle of the douche product of FIG. 1.

FIG. 6 is an exploded perspective view of the douche product of FIG. 1 illustrating assembly of the nozzle on the container.

FIG. 7 is a sectional view of a douche nozzle formed in accordance with a modification of the first embodiment.

FIG. 11 is a perspective view of a disposable douche product formed in accordance with a second embodiment of this invention.

FIG. 12 is a perspective view of a disposable douche product formed in accordance with a third embodiment of this invention.

FIG. 13 is a partial sectional view of the third embodiment illustrating the position of the nozzle as it is being mounted onto the container.

FIG. 14 is a partial sectional view of the third embodiment illustrating the position of the nozzle when it is mounted on the container.

FIG. 15 is a perspective view of a disposable douche product formed in accordance with a fifth embodiment of this invention.

FIG. 16 is an enlarged side view of the nozzle of the fifth embodiment illustrating in phantom lines its mating relationship with the liquid container.

FIG. 17 is a perspective view of the fifth embodiment illustrating the nozzle being removed from the container.

DETAILED DESCRIPTION OF THE INVENTION

Figure 1:
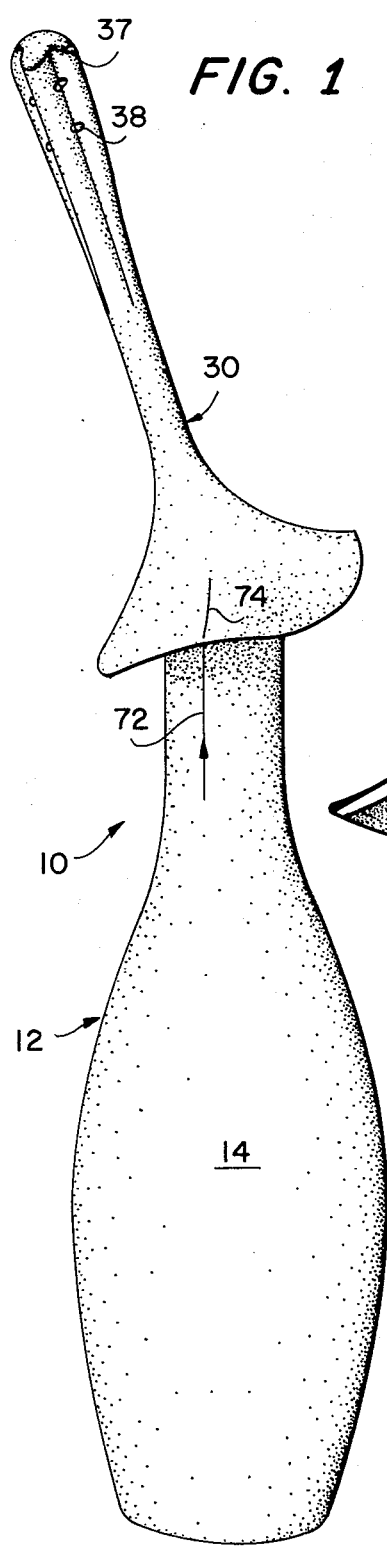
FIG. 1 is a perspective view of a disposable douche product formed in accordance with a first embodiment of this invention.

Reference will now be made in detail to present preferred embodiments of the invention, examples of which are illustrated in the accompanying drawings. Terms of orientation used throughout the specification and claims, such as upper and lower, top and bottom, are used with reference to the douche product orientation as shown in the drawings for simplification of description and are not intended to have any limiting connotation.

Referring now to the drawings, and particularly FIGS. 1–6, there is illustrated a disposable douche product formed in accordance with a first embodiment of this invention and which includes two independent elements, namely a liquid container and a dispensing pipe or nozzle. As here embodied, a disposable douche product 10 includes a flexible container 12 having a body 14, preferably elongated, a generally cylindrical neck 16 formed adjacent one end thereof and a head 18 formed on the neck and spaced from the container body 14. The bottom of the head 18 is larger than the neck 16 to provide a retaining wall for the nozzle as is described below. One suitable shape for the head is a conical frustum as shown. The container body 14, neck 16, and head 18 are formed as one integral unit. The container body 14 must be flexible to permit the user to easily squeeze the body in order to eject the douching solution contained therein. However, because the nozzle is to be snap-fitted onto the container head 18, the head and supporting neck 16 are provided with greater rigidity than the container body 14.

The neck 16 and head 18 are hollow thereby forming a fluid-flow passageway 20 therein which communicates with the interior of the container body 14 to provide a passageway through which a liquid may be ejected from the container 12. A plug 22 is integrally formed on the end of the head 18 in order to seal the passageway 20 to prevent the liquid from being expelled from the container 12 until desired. The plug 22 is intended to be easily removed by the user. To facilitate easy removal of the plug 22, the wall thickness at the point where the plug 22 joins the head 18 is provided with a weakened or tear section 24. Furthermore, the plug is formed with a transversely extending projection or handle 26 so that the user can easily grasp the plug and by rotating or twisting the handle the plug will be easily torn from the head 18 thereby exposing the passageway 20 to permit the liquid within the container 12 to be ejected by squeezing the container body 14. Of course, the plug 22 can also be removed by cutting it with a sharp instrument, such as a scissors or knife.

Enough douching solution or liquid for one application is loaded into the container 12 and sealed therein by the plug 22 as described above. The loading and sealing can be accomplished by conventional equipment presently available; however, a preferred method for producing and loading the container 12 is to simultaneously blow mold and fill the container such as with a machine of the type disclosed in U.S. Pat. No. 3,325,860, the disclosure of which is incorporated herein. Polyethylene, or other conventional plastic materials, are suitable for forming the container 12.

Figure 4:
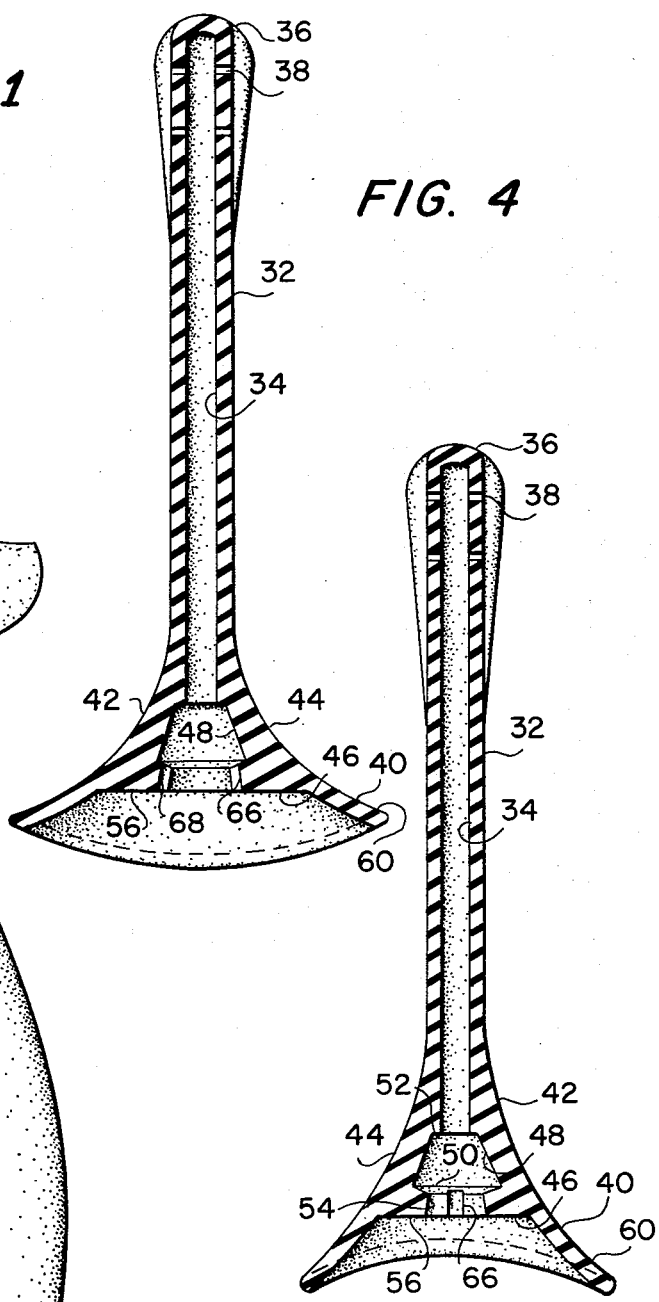
FIG. 4 is a sectional view taken along line 4—4 of FIG. 3.
Figure 3:
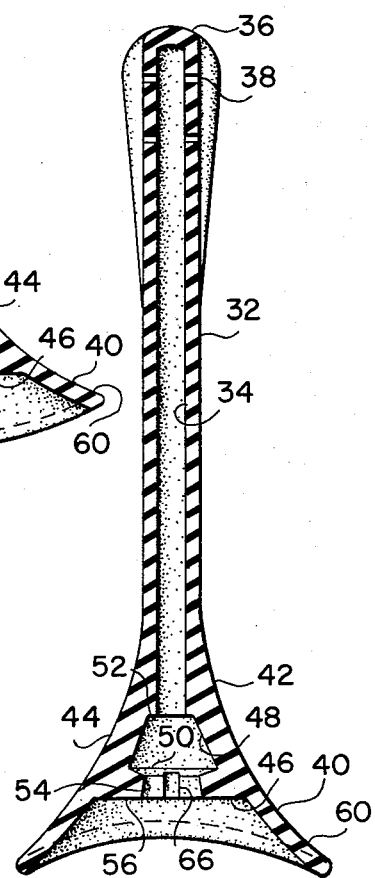
FIG. 3 is a cross-sectional view of the nozzle of the douche product of FIG. 1 taken along line 3—3.

In accordance with this invention, a douche pipe or nozzle 30, as shown in detail in FIGS. 3–5, is adapted to be used together with the container 12 by mounting the nozzle 30 onto the head 18 of the container 12. The nozzle 30 includes an elongated, flexible tube 32 having a passageway 34 along the length thereof. Preferably, the exterior surface of the distal end 36 of the nozzle is formed with recessed sections, such as through the use of a generally cruciform shape 37 (see FIG. 1). A plurality of apertures 38 are provided through the distal end 36 of the nozzle 30 and communicate with the passageway 34. The apertures are located in the recessed sections of the cruciform 37 in order to prevent the apertures 38 from becoming obturated during use.

The proximate end 40 of the nozzle 30 is provided with a base portion 42 which is formed with a diverging exterior wall 44 as can be seen in FIGS. 3 and 4. Preferably, the base portion 42 has a generally conical configuration or, more specifically, is in the form of an ellipical hyperboloid. This configuration provides a contour which is suitably adapted for a close and comfortable anatomical fit. The base portion 42 terminates with a bottom wall 46.

Means are provided within the base portion 42 to permit relatively easy attachment of the nozzle 30 onto the container 12. To accomplish this attachment, there is provided a conical frustum shaped cavity 48 within the base portion 42 which conforms in shape to the container head 18. The cavity 48 is oriented so that the major or larger base 50 thereof is adjacent to the bottom wall 46 while the minor base 52 is remote from the bottom wall 46. A passageway 54, which is preferably tapered in a direction toward the distal end 36 of the nozzle 30, is formed through the bottom wall 46 of the base portion 42 and communicates with the cavity 48. The diameter of the passageway 54 is smaller than the diameter of the base 50 of the frustum cavity 48 thereby forming a retaining ring 56 between the bottom wall 46 and the cavity 48.

Further in accordance with this invention, the nozzle 30 is provided with a shield portion 60 integrally formed on the proximate or bottom end of the nozzle 30. The shield portion 60 is formed as a continuation of the diverging wall 44, and projects downwardly below the bottom wall 46. Both the major and minor diameters of the elliptical shield portion 60 are larger than the diameter of container 12. The wall thickness of the nozzle tube 32 and the shield portion 60 is less than the wall thickness of the base portion 42 thereby providing the tube and the shield with greater flexibility than the base portion. This configuration provides the base portion 42 with sufficient rigidity to permit easy mounting of the nozzle 30 onto the container 12 while still providing appropriately soft and flexible characteristics to the tube 32 and shield 60 to enable the tube and shield to readily and comfortably adapt themselves to the distinctive angles, size and contour of the individual using the douche product 10 of this invention.

The nozzle 30 is designed to be easily molded of a flexible, inexpensive plastic, for example polyvinylchloride.

The sealed container 12 containing the douching liquid and the nozzle 30 are packaged together with the nozzle not being mounted on the container 12. Of course, the container 12 or the nozzle 30 can be sold as separate units. To use the douche product 10 of this invention, the user grasps the plug 22 and twists it in order to sever the plug from the distal end of the container 12 thereby exposing the passageway 20 through the head 18 (see FIG. 6). The user then takes the nozzle 30 and forces the base portion 42 downwardly onto the head 18 until the retaining ring 56 snaps over the bottom of the conical head 18 and about the neck 16 thereby retaining the nozzle 30 on the container 12. The diverging walls of the base portion 42 and the shield portion 60 serve as a handle to facilitate the mounting of the nozzle 30 onto the container head 18. The user then gently inserts the nozzle 30 into the body cavity and squeezes the container 12 in order to eject the liquid from the container, through the passageway 20 in the head 18 into the passageway 34 in the nozzle 30 and out through the apertures 38 into the body cavity. The liquid will then naturally flow out of the body cavity and be directed downwardly and away from the user's legs and hand by the projective shield portion 60.

As can be observed in FIG. 2, the head 18 of the container 12 of this first embodiment forms an obtuse angle with the longitudinal axis of the container 12, such as a 135° angle. This angled orientation permits the use of a straight nozzle tube 32 while providing a proper angular relationship between the nozzle tube 32 and the container body 14 to allow the user to comfortably and conveniently hold the container 12 and insert the nozzle 30 into the body cavity.

To ensure that the nozzle 30, particularly the shield 60, is properly oriented with respect to the container 12 to facilitate simple and comfortably use of the douche product 10, there is provided cooperating alignment means on the container head 18 and the nozzle base portions 42. While various types of alignment means can be employed, one particular alignment means, as illustrated in FIGS. 2-5, includes a pair of diametrically opposed alignment keys 62, 64 formed on the neck 16 of the container 12 adapted to mate with a pair of diametrically opposed cooperating alignment keyways 66, 68 respectively, formed in the base portion 42 of the douche nozzle. The alignment means ensures that the nozzle 30 is mounted onto the container 12 so that the major axis of the elliptical base portion 42 and shield portion 60 is co-planar with a plane parallel to the plane of paper of FIG. 2 and bisecting the container head 18. To facilitate the user to achieve this orientation, an alignment arrow and line 72 are provided on the container body 14 adjacent to the head 18 and neck 16 and a matching line 74 is provided along the major axis on the nozzle shield and base.

In a modified form of this first embodiment, illustrated in FIG. 7, the douche nozzle 80 is shown having substantially the identical structure as the nozzle 30 shown in FIGS. 1 and 3–6. However, the base portion 82, in addition to being provided with a conical frustum cavity 84 adapted to receive the head 18 of a container 12, is also provided with an additional cavity 86 in which is mounted a flow control or check valve. While various types of check valves can be used, a preferred form is a disphragm 88 having a slit therein which opens only when pressure on the container side of the diaphragm 88 exceeds the pressure on the nozzle tube side of the diaphragm. The check valve 88 permits liquid flow in one direction, namely through a passageway 90 in the base portion 82 into the passageway 92 extending through the elongated, flexible tube 94 and out through the apertures 96 at the distal end of the nozzle 80 while preventing the flow in the reverse direction. Another example of a suitable check valve is a flapper valve (not shown).

Figure 8:
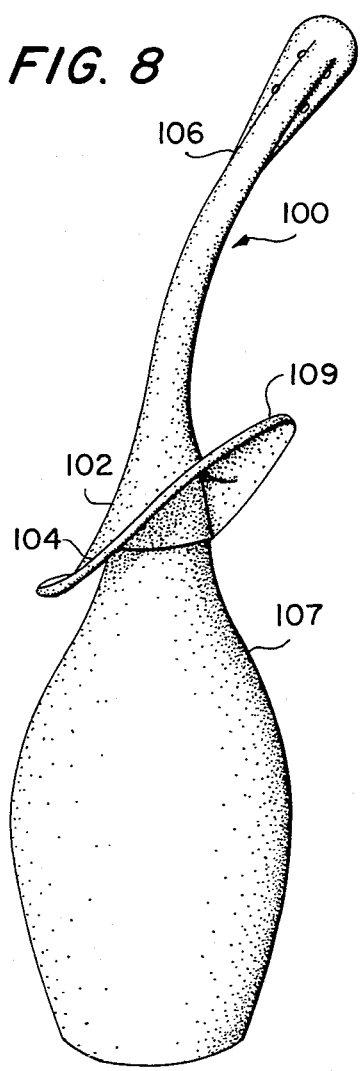
FIG. 8 is a perspective view of a disposable douche product formed in accordance with a second embodiment of this invention.
Figure 9:
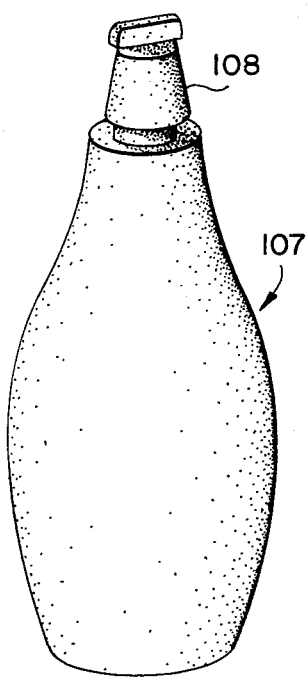
FIG. 9 is a perspective view of the liquid container of the douche product of FIG. 8.
Figure 10:
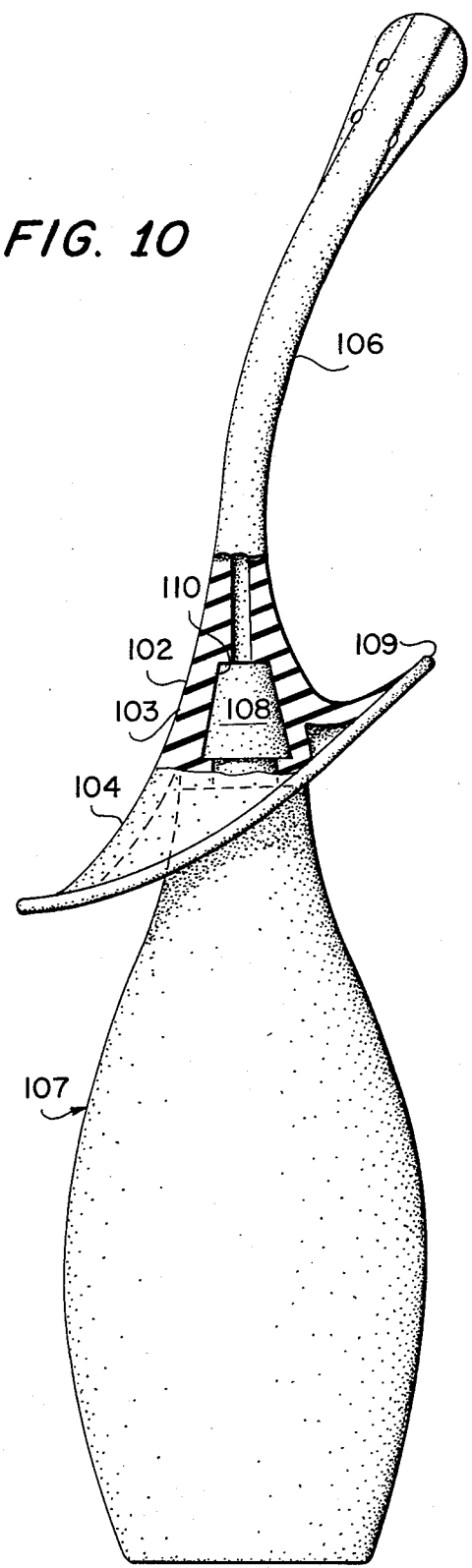
FIG. 10 is a partial sectional view of the douche product of FIG. 8.

FIGS. 8–10 illustrate a second embodiment of this invention involving a modified configuration of the nozzle base and shield portion. In accordance with this invention, the nozzle 100 is formed with a generally elliptical base 102 having a diverging wall 103 which terminates in a shield portion 104 which also has a generally elliptical contour. In order to allow a closer anatomical fit, the shield 104 is provided with a generally saddle like curvature in the direction parallel to a plane through the major axis of the elipse as can be seen in FIGS. 8 and 10.

Another feature illustrated in this embodiment is the use of a curved or concavo-convex, elongated tube 106 designed to be used in conjunction with a container 107 having a head 108 which is oriented axially with respect to the longitudinal axis of the container 107. The tube 106 is curved toward the higher edge 109 of the shield portion 104, both of which are intended to face the frontal portion of the user's body. This configuration may be contrasted with the configuration shown in FIGS. 1–7 wherein the head 18 is positioned at an obtuse angle with respect to the longitudinal axis of the container 12 and the nozzle tube 94 is generally straight. A cavity 110 formed in the base 102 conforms in shape to the container head 108 for a snap-on attachment as described above with respect to the first embodiment.

A further modification of this invention is illustrated in FIG. 11 wherein a douche nozzle 120 includes an eccentric shield 122 which overlaps one side of a liquid container 124, namely, the side of the container intended to face the frontal portion of the user's body. The shield, as before, functions as a handle for facilitating attaching the nozzle 120 to the container 124 and for removing it from the container 124, as well as for directing the flow of the effluent away from the external parts of the user's body and downwardly into a disposal drain, such as a toilet bowl or bathtub.

A fourth embodiment of this invention is illustrated in FIGS. 12–14 wherein a disposable douche product 130 includes a container 132 and a nozzle 134 having a different type of means for attaching the nozzle to the container. The nozzle 134 is formed with a base portion 136 having a diverging exterior wall 137 which continues into the formation of a shield portion 138 having an elliptical cross-sectional configuration. A cavity 139, having a mating shape with the head 140 of the container 132, is formed in the nozzle base 136 forming a retaining ring 142 for gripping the underside of the container head 140.

However, in the present embodiment, instead of snapping the nozzle 134 onto the head 140 of the container 132 in the manner disclosed in connection with the embodiments described above, the nozzle 134 is mounted on the container 132 by inverting the shield portion 138 relative to the base 136 so that it faces the distal end 144 of the nozzle 134 (FIG. 13). Such an inversion of the shield portion 138 causes the retaining ring 142 to spread and allows the nozzle 134 to be easily placed upon the container head 140 so that the head fits within the cavity 139 provided in the base of the nozzle 134. The shield portion 138 is then pressed downwardly so that it snaps back into its normal, downwardly disposed position as can be seen in FIG. 14 wherein the retaining ring 142 snaps into place below the container head 140 and around the container neck 148, providing firm retention. This attachment means permits mounting the nozzle 134 onto the container 132 with a minimal amount of pressure on the container 132, which is advantageous in view of the flexible nature of the container.

In order to remove the nozzle 134 for reuse or disposal, the shield is again inverted and the nozzle 134 is easily removed from the container 132.

A fifth embodiment of this invention is disclosed in FIGS. 15–17 and includes a douche product 150 comprising a nozzle 152 and container 154 wherein the shield portion 156 of the nozzle is not spaced from the container 154 when mounted on the container 154, as it is in the four embodiments described above. One side 157 of the generally elliptical shield 156 extends downwardly along a portion of the length of the container 154 further than does the diametrically opposite side 158 of the shield 156. The longer side 157 is intended to be the front or upper side of the douche product 150 when in use, or, in other words, intended to face the frontal portion of the user's body. The shield 156 will prevent the effluent from flowing around the entire container 154 and will direct the effluent downwardly into a drain thereby preventing the effluent from contacting the user's legs and hand.

The nozzle 152 is provided with a cavity 159 conforming in shape and size to the container head 160 and, as with the aforedescribed embodiments, a retaining ring 162 is formed below the cavity 159. The nozzle 152 is removably mounted on the head 160 of the container 154 by holding the nozzle 152 at an angle relative to the head 160 so that the portion of the nozzle retaining ring 162 which is formed on the short side 158 of the shield 156 is placed about the neck 164 of the container 154. By grasping the longer side of the shield 156 and pulling it downwardly over the head 160, the remainder of the retaining ring 162 will gradually enclose around the container neck 164 until the nozzle 152 is mounted on the container 154. The nozzle is removed in the reverse manner by grasping the longer side 157 of the shield 156 and gradually stripping the nozzle 152 off of the container 154 as is shown in FIG. 17.

It can be seen that the douche product of this invention provides a completely self-contained and disposable douche product which is ready for use and which includes an improved nozzle which has a flow directing shield integrally formed as an integral part thereof. The shield allows for a more protective spill-out control for the user and also functions as a handle for facilitating attaching the nozzle to a container and removing it from the container, as well as providing a comfortable and close anatomical fit. Provision is also made for the use of a check valve, if desired. While the check valve is shown for use only in the first embodiment, it is clear that all of the five embodiments described above can be modified to include such a check valve.

What is claimed is:

1. A douche nozzle adapted to be attached to a liquid container comprising:
   a flexible, elongated tube having a passageway therethrough, at least one aperture through a first end of said tube communicating with said passageway and formed to direct liquid flowing outwardly of the container through said passageway substantially transversely of the long axis of said tube, and
   a liquid effluent flow-directing combined base and shield formed at a second end of said tube remote from said first end, the axial extent of said tube extending from said combined base and shield being at least twice the axial extent of said combined base and shield, the intersection of the exterior surface of said combined base and shield and a plurality of planes through the longitudinal axis of said nozzle and spaced about the periphery of said nozzle each defines a continuous concave curve having a predetermined radius of curvature,
   the base portion having a substantially concial configuration, a bottom wall and means adapted to sealingly affix said base portion on a liquid container,
   a flexible shield portion having at least a section thereof extending away from said first end and beyond said bottom wall and adapted to overlap the container when mounted thereon, said combined base and shield directing the flow of effluent which has left the nozzle downwardly substantially perpendicularly to the longitudinal axis of said nozzle.

2. A douche nozzle as defined in claim 1 wherein said means to affix said base portion onto a container comprises a cavity within said base portion and means for releasably retaining said base portion on said container.

3. A douche nozzle as defined in claim 2 including a second cavity within said base portion and a check valve mounted within said second cavity.

4. A douche nozzle as defined in claim 1 wherein said means to affix said base portion onto a container comprises a cavity within said base portion and a retaining ring and wherein the flexibility of said baase portion is substantially less than the flexibility of said tube.

5. A douche nozzle as defined in claim 1 wherein said tube and shield portion have greater flexibility than said base portion.

6. A douche nozzle as defined in claim 5 wherein said wall thickness of said base portion is greater than the wall thickness of said tube and said shield portion.

7. A douche nozzle as defined in claim 1 including alignment means on said base portion adapted to cooperate with mating alignment means on said container in order to facilitate proper orientation of said shield portion relative to said container.

8. A douche nozzle as defined in claim 2 and including a second cavity within said said base and a check valve mounted within said second cavity to permit fluid flow in a first direction through said passageway and out through said aperture and to preclude fluid flow through said passageway in a second direction opposite to said first direction.

9. A douche nozzle as defined in claim 1 wherein said tube has a concavo-convex curvature along its length.

10. A douche nozzle as defined in claim 1 wherein said base portion and shield portion each have a generally elliptical cross-section in a plane normal to an axis through said passageway.

11. A douche nozzle as defined in claim 10 wherein the edge of said shield remote from said base is continuously curved, wherein the major axis of said elliptical cross section intersects opposite curved edges of said shield lying in a first plane normal to the axis of said passageway at a location spaced between said base and a parallel second plane containing the minor axis of said elliptical cross section and wherein said minor axis intersects the opposite curved edges of said shield.

12. A douche nozzle as defined in claim 11 wherein said first end of said tube is cruciform in cross section in a plane normal to the axis of said tube with the margins about said aperture disposed between the projections forming said cruciform cross section, alignment means on said base portion adapted to cooperate with mating alignment means on the container in order to facilitate proper orientation of said shield portion relative to the container, said base portion being in the form of an elliptical hyperboloid.

13. A douche nozzle as defined in claim 1 wherein said shield portion extends from said base portion and less than 360° around said base portion.

14. A disposable douche product comprising:
 a. a flexible, squeezable, container having a head at one end thereof, a first passageway through said head, removable means on said head obturating said first passageway,
 b. a douching liquid contained within said container, at substantially atmospheric pressure, the quantity of said liquid being suitable for a single douching application, and
 c. a nozzle including
  i. an elongated flexible tube having a second passageway therethrough, at least one aperture through a distal end of said tube communicating with said second passageway, the proximate end of said tube including a base portion having a substantially conical configuration,
  ii. means in said base portion adapted for releasable mounting on said container head when said removable means is removed from said head, and
  iii. a flexible shield portion formed as a continuation of said base portion, removal of said removable means from said container and mounting of said base portion on said head effects fluid flow communication between said first and second passageways and effects said shield portion overlapping a portion of said container, said base and shield portions directing the flow of effluent which has left the nozzle downwardly substantially perpendicularly to the longitudinal axis of said nozzle,
  iv. the axial extent of said tube extending from said base portion being at least twice the axial extent of said base portion and said shield portion, said aperture being formed to direct liquid outwardly of said container through said passageways substantially transversely of the long axis of said tube.

15. A disposable douche product as defined in claim 14 wherein said head includes a neck extending from said container and a conical frustum at the end of said neck and spaced from said container, the major base of said frustum having a larger diameter than said neck, wherein said base portion includes a bottom wall and wherein the mounting means in said base portion includes a conical frustum cavity within said base portion and spaced from the bottom wall to form a retaining ring between the major base of the frustum cavity and the bottom wall, the cavity being adapted to receive the container head frustum and the retaining ring being adapted to snap onto the container neck in order to retain the nozzle and shield on the container.

16. A disposable douche product as defined in claimm 14 wherein the base portion and head include cooperating alignment means to facilitate mounting said base portion onto said head with a predetermined orientation.

17. A disposable douche product as defined in claim 14 wherein said container is elongated and said container head forms an oblique angle with the longitudinal axis of said container.

18. A disposable douche product as defined in claim 14 wherein said tube and shield portion have greater flexibility than said base portion.

19. A disposable douche product as defined in claim 14 wherein the base portion and shield portion have a substantially elliptical cross-sectional configuration in a plane perpendicular to the longitudinal axis of said tube.

20. A disposable douche product as defined in claim 14 wherein the shield portion is spaced from the exterior surface of said container.

21. A disposable douche product as defined in claim 20 wherein said tube and shield portion have greater flexibility than said base portion.

22. A disposable douche product as defined in claim 14 wherein said elongated tube has a concavo-convex curvature along its length.

23. A douche nozzle as defined in claim 1 including alignment means on said base portion adapted to cooperate with mating alignment means on the container in order to facilitate proper orientation of said shield portion relative to the container, said base portion and said shield portion each having a generally elliptical cross section in a plane normal to an axis through said passageway, said base portion being in the form of an elliptical hyperboloid.

24. A douche nozzle as defined in claim 1 wherein said tube has a shank portion extending from said base portion, said first tube end being enlarged at least in one transverse direction relative to the largest transverse extent of said shank portion, the margins about said aperture being recessed from the surface of said enlarged tube end.

25. A douche nozzle as defined in claim 24 wherein said enlarged tube end is cruciform in cross section in a plane normal to the axis of said tube with the margins about said aperture disposed between the projections forming said cruciform cross section, alignment means on said base portion adapted to cooperate with mating alignment means on the container in order to facilitate proper orientation of said shield portion relative to the container, said base portion and said shield portion each having a generally elliptical cross section in a plane normal to an axis through said passageway, said base portion being in the form of an elliptical hyperboloid.

26. A disposable douche product comprising:
 a. a flexible squeezable container having a head at one end thereof, a first passageway through said head, removable means on said head obturating said first passageway, b. said head forming an oblique angle with the longitudinal axis of said container, c. a douching liquid contained within said container at substantially atmospheric pressure, the quantity of said liquid being suitable for a single douching application, and d. a nozzle including:
  i. an elongated tube having a second passageway therethrough, at least one aperture through a distal end of said tube communicating with said second passageway, the proximate end of said tube including a base portion,
  ii. means in said base portion adapted for releasable mounting on said container head when said removable means is removed from said head.

27. A disposable douche product as defined in claim 26, wherein said head includes a neck extending from said container and a conical frustum at the end of said neck and spaced from said container, the major base of said frustum having a larger diameter than said neck, wherein said base portion includes a bottom wall and wherein the mounting means in said base portion includes a conical frustum cavity within said base portion and spaced from the bottom wall to form a retaining ring between the major base of the frustum cavity and the bottom wall, the cavity being adapted to receive the container head frustum and the retaining ring being adapted to snap onto the container neck in order to retain the nozzle on the container.

28. The disposable douche product as defined in claim 26 wherein the base portion and head include cooperating alignment means to facilitate mounting said base portion onto said head with a predetermined orientation.

29. The disposable douche product as defined in claim 26 wherein said elongated tube has a concave-convex curvature along its length.

30. The disposable douche product as defined in claim 26 wherein said means for mounting said base portion on said container head comprises a cavity within said base portion and means for releasably retaining said base portion on said container.

31. The disposable douche product as defined in claim 26 wherein said elongated tube is straight and said head forms an oblique 135° angle with the longitudinal axis of said container.

32. A disposable douche product as defined in claim 26 including a flexible shield portion formed as a continuation of said base portion, removal of said removable means from said container and mounting of said base portion on said head effects fluid flow communication between said first and second passageway and effects said shield portion overlapping a portion of said container, said base and shield portions directing the flow of effluent which has left the nozzle downwardly substantially perpendicular to the longitudinal axis of said nozzle, said container being elongated and said container head forming an oblique angle with the longitudinal axis of said container, said tube extending from said container when said nozzle is mounted thereto such that the axis of said tube and the longitudinal axis of said container from an obtuse angle one with the other.

33. A disposable douche product as defined in claim 32 wherein said base portion and said shield portion each have a generally elliptical cross section in a plane normal to the axis of said tube, said base portion and said head including cooperating alignment means to facilitate mounting said base portion onto said head with the major axis of said elliptical cross section lying substantially in a plane containing the axis of said tube and the longitudinal axis of said container.

34. A disposable douche product comprising:

a. a flexible squeezable container having a head at one end thereof, a first passageway through said head, removable means on said head obturating said first passageway, b. said head forming an oblique angle with the longitudinal axis of said container, c. a douching liquid contained within said container at substantially atmospheric pressure, the quantity of said liquid being suitable for a single douching application, and d. a nozzle including:
  i. an elongated flexible tube having a second passageway therethrough, at least one aperture through a distal end of said tube communicating with said second passageway, the proximate end of said tube including a base portion,
  ii. means in said base portion adapted for releasable mounting on said container head when said removable means is removed from said head, and
  iii. a flexible shield portion formed as a continuation of said base portion, removal of said removable means from said container and mounting of said base portion on said head effects fluid flow communication between said first and second passageways and effects said shield portion overlapping a portion of said container, said base and shield portions directing the flow of effluent leaving the nozzle downwardly substantially perpendicularly to the longitudinal axis of said nozzle.

35. The disposable douche product as defined in claim 34 wherein said elongated tube is straight and said head forms an oblique 135° angle with the longitudinal axis of said container.

36. A disposable douche product according to claim 34 wherein said tube extends from said container when said nozzle is mounted thereto such that the axis of said tube and the longitudinal axis of said container form an obtuse angle one with the other, said base portion and said shield portion each having a generally elliptical cross section in a plane generally normal to the axis of said tube, said base portion and said head including cooperating alignment means to facilitate mounting said base portion onto said head with the major axis of said elliptical cross section lying substantially in a plane containing the axis of said tube and the longitudinal axis of said container.

37. A disposable douche product according to claim 34 wherein said base portion and said shield portion each have a generally elliptical cross section in a plane normal to an axis through said second passageway.

38. A disposable douche product according to claim 37 wherein the edge of said shield remote from said base is continuously curved, wherein the major axis of said elliptical cross section intersects opposite curved edges of said shield lying in a first plane normal to the axis of said passageway at a location spaced between said base and a parallel second plane containing the minor axis of said elliptical cross section and wherein said minor axis intersects the opposite curved edges of said shield.

39. A disposable douche product comprising:
  a flexible, squeezable container having a head at one end thereof, a first passageway through said head, said container being elongated and said head forming an oblique angle with the longitudinal axis of said container, a douching liquid contained within said container, the quantity of said liquid being suitable for a single douching application, an elongated tube mounted on said head and having a second passageway therethrough, at least one aperture through a distal end of said tube communicating with said second passageway, a shield adjacent said head, at least a portion of said shield extending away from said head toward the bottom of said container and spaced from the exterior surface of said container, said shield directing the flow of effluent which has left the tube downwardly perpendicularly to the longitudinal axis of said container.

40. A disposable douche product according to claim 39 wherein said tube extends from said container such that the axis thereof and the longitudinal axis of said container form an obtuse angle one with the other.

41. A disposable douche product comprising:
an elongated flexible, squeezable container having a head at one end thereof, a first passageway through said head,
a douching liquid contained within said container at substantially atmospheric pressure, the quantity of said liquid being suitable for a single douching application,
an elongated tube carried by said head and having a second passageway therethrough, a least one aperture through a distal end of said tube communicating with said second passageway, said tube extending from said container such that the axis of said tube and the longitudinal axis of said container form an obtuse angle one with the other,
a shield adjacent said head, at least a portion of said shield extending away from said head toward the bottom of said container and spaced from the exterior surface of said container, said shield directing the flow of effluent which has left the tube downwardly substantially perpendicular to the longitudinal axis of said container.

42. A douche product according to claim 41 wherein said shield has a generally elliptical cross section in a plane generally normal to the axis of said tube, said shield being oriented relative to said tube and said container such that the major axis of said elliptical cross section lies substantially in a plane containing the axis of said tube and the longitudinal axis of said container.

43. A douche product according to claim 42 wherein the axial extent of said tube extending from said shield is at least twice the axial extent of said shield.

44. A disposable douche product comprising:
a. a flexible, squeezable, container having a head at one end thereof, a first passageway through said head, removable means on said head obturating said first passageway,
b. a douching liquid contained within said container, at substantially atmospheric pressure, the quantity of said liquid being suitable for a single douching application, and
c. a nozzle including
  i. an elongated flexible tube having a second passageway therethrough, at least one aperture through a distal end of said tube communicating with said second passageway, the proximate end of said tube including a base portion having a substantially conical configuration,
  ii. means in said base portion adapted for releasable mounting on said container head when said removable means is removed from said head, and
  iii. a flexible shield portion formed as a continuation of said base portion, removal of said removable means from said container and mounting of said base portion on said head effects fluid flow communicating between said first and second passageways and effects said shield portion overlapping a portion of said container, said base and shield portions directing the flow of effluent which has left the nozzle downwardly substantially perpendicularly to the longitudinal axis of said nozzle,
the base portion and head including cooperating alignment means to facilitate mounting said base portion onto said head with a predetermined orientation, said container being elongated and said container head forming an oblique angle with the longitudinal axis of said container.

45. A disposable douche product as defined in claim 44 wherein said tube extends from said container when said nozzle is mounted thereto such that the axis of said tube and the longitudinal axis of said container form an obtuse angle one with the other.

46. A disposable douche product as defined in claim 45 wherein said base portion and said shield portion each have a generally elliptical cross section in a plane normal to the axis of said tube, said base portion and said head including cooperating alignment means to facilitate mounting said base portion onto said head with the major axis of said elliptical cross section lying substantially in a plane containing the axis of said tube and the longitudinal axis of said container.

* * * * *

UNITED STATES PATENT OFFICE
CERTIFICATE OF CORRECTION

Patent No. 3,968,797      Dated July 13, 1976

Inventor(s) GILBERT PACKER, et al.

It is certified that error appears in the above-identified patent and that said Letters Patent are hereby corrected as shown below:

Claim 4, line 4, the word "baase" should read --base--.

Claim 8, line 2, the word "said" in the second instance should be deleted.

Claim 16, line 2, the word "claimm" should read --claim--.

Claim 44 (c)(iii), line 24, the word "communicating" should read --communication--.

Signed and Sealed this

Eighteenth Day of January 1977

[SEAL]

Attest:

RUTH C. MASON
*Attesting Officer*

C. MARSHALL DANN
*Commissioner of Patents and Trademarks*